United States Patent [19]
Geimer

[11] Patent Number: 6,053,368
[45] Date of Patent: Apr. 25, 2000

[54] ANTI-CONTAMINATION DISPENSING APPARATUS FOR FLUIDS

[75] Inventor: Günter Geimer, Schönenberg-Kübelberg 2, Germany

[73] Assignee: Ursatec Verpackung-GmbH, Homburg, Germany

[21] Appl. No.: 09/068,801
[22] PCT Filed: Oct. 8, 1996
[86] PCT No.: PCT/EP96/04356
§ 371 Date: Sep. 10, 1998
§ 102(e) Date: Sep. 10, 1998
[87] PCT Pub. No.: WO97/18902
PCT Pub. Date: May 29, 1997

[30] Foreign Application Priority Data

Nov. 17, 1995 [DE] Germany ............................ 195 42 959
Mar. 13, 1996 [DE] Germany ............................ 196 09 880

[51] Int. Cl.$^7$ ...................................................... B67D 5/58
[52] U.S. Cl. .................................. 222/189.09; 222/321.1; 222/321.6; 222/321.7; 222/321.9; 141/285
[58] Field of Search ........................... 222/189.09, 321.1, 222/321.6, 321.7, 321.9; 141/285

[56] References Cited

U.S. PATENT DOCUMENTS

| 3,333,741 | 8/1967 | Radcliffe | 222/189.09 |
| 4,054,139 | 10/1977 | Crossley | 128/260 |
| 4,694,976 | 9/1987 | Schuetz | 222/189.09 |
| 4,722,731 | 2/1988 | Vailancourt | 604/122 |
| 4,973,320 | 11/1990 | Brenner et al. | 604/265 |
| 5,154,325 | 10/1992 | Ryder et al. | |
| 5,232,687 | 8/1993 | Geimer | |
| 5,927,559 | 7/1999 | Bommer et al. | 222/189.09 |

FOREIGN PATENT DOCUMENTS

| 3-240655 | 10/1991 | Japan | 222/189.09 |
| WO94/11115 | 5/1994 | WIPO | |

Primary Examiner—Henry J. Recla
Assistant Examiner—Khoa Huynh
Attorney, Agent, or Firm—Scully, Scott, Murphy & Presser

[57] ABSTRACT

A dispensing apparatus for fluids from a storage vessel in which air flows into the storage vessel (1) while the fluid is being dispensed to compensate pressure. In this dispensing apparatus is provided, filters for sterilizing, degerminating or reducing germs are provided in the air intake area and, separately from this, filters for sterilizing, degerminating or reducing germs in the fluid are provided in at least one part of the fluid outlet. This means that a dispensing apparatus can be provided which can be adapted to available conventional storage vessels and filling systems, and which efficiently protects the fluid in the storage vessel from becoming contaminated at reasonable costs so that the use of preservatives is rendered unnecessary. This dispensing apparatus can be a pump (2) or it can be formed such that the storage vessel is a squeezy bottle (31).

9 Claims, 2 Drawing Sheets

ANTI-CONTAMINATION DISPENSING APPARATUS FOR FLUIDS

The invention relates to dispensing apparatus for fluids in which air flows back to effect pressure compensation according to the preamble of claim 1.

Conventional dispensing apparatus or metering pumps for pharmaceuticals and cosmetics are known. Such dispensing apparatus are mounted on a storage vessel for the fluid which is to be dispensed. In order to prevent a partial vacuum from being created in the storage vessel when the fluid is dispensed, ambient air flows into the storage vessel. The drawback of such dispensing apparatus is that the incoming air contains germs and therefore contaminates the fluid in the storage vessel. Furthermore, the fluid becomes contaminated at the outlet as a result of contact with the surroundings. This contamination can intermingle with the stored fluid in the storage vessel during the fluid's path to the outlet and also contaminate this fluid. In the case of pharmaceuticals and cosmetics, such a contamination leads to spoiled goods and danger for the user.

For this reason, so-called "airless systems" have been developed in which pressure compensation in the storage vessel is unnecessary, i.e. ambient air does not have to flow into the storage vessel. This is achieved by a special type of storage vessel. There are storage vessels with drag pistons in which the volume of the storage vessel is reduced during dispensing of the fluid by means of a drag piston. The drawback is that only cylindrical storage vessels can be used. Furthermore, there are also double-walled storage vessels in which the stored fluid is located in a ductile inner bag and incoming ambient air is taken up for pressure compensation between a fixed outer vessel and a workable inner vessel. There are also storage vessels in which germ-free air is taken up under increased inner pressure. The drawback of all these systems is that a special receptacle is required for the dispensing apparatus. This makes the system very expensive to produce and means that it cannot be adapted to conventional storage vessels and filling systems already available. Furthermore, such a system is also very expensive so it is not possible to use it for pharmaceuticals and cosmetics in the lower price range without employing preservatives. Irrespective of the price range of the products, preservatives entail harmful effects for the consumer. They are dubious substances and lead to undesireable side effects.

The object underlying the invention is to provide an apparatus of the type mentioned above for the repeated dispensing of fluids from a store with pressure compensation being obtained by means of air which protects the stored fluid from being contaminated with germs and thus renders the use of preservatives unnecessary.

A further object of the present invention is to provide a dispensing apparatus for fluids which can be adapted to conventional storage vessels and which can be produced at reasonable costs.

This object is achieved by the features claimed in claim 1.

Further embodiments are revealed by the subclaims.

The present invention uses a fluid dispensing apparatus in which the path of the fluid to the outlet is guided, at least in one part, separately from the air inlet path for the air which is intended to reach the supply vessel for pressure compensation. In this way, the air-borne germs and fluid germs can be made ineffective separately from one another. This has the advantage that different methods can be used for degerminating the fluid and the air, each of which methods can be adapted to the different needs. The degermination of or the reduction in germs in the fluid occurs in the region of the fluid's outward path by means of oligodynamically effective substances. Heavy metals and/or heavy metal alloys in metallic and/or ionic form can be used. The use of silver has proven particularly favourable. The degermination or reduction of germs in the fluid in the area of the fluid's path to the outlet has the effect that no germs from the outlet coming into contact with the surroundings can pass past the valve against the flow of the fluid (e.g. by proliferation) to reach the storage vessel and that the germ-free fluid from the storage vessel is not contaminated by contaminated residue (e.g. on the outlet) when dispensed which would make the microbiological quality of the product the consumer obtains questionable. In addition, the growth of germs on the outlet and in all regions of the dispensing apparatus is prevented, in particular in the case of a pump or a valve.

The degermination of the air flowing into the storage vessel to compensate pressure can also be achieved by other methods suited to dealing with air-borne germs. Thus, the air can be guided through a sterile filter on its way into the apparatus or can pass into the storage vessel after permeation by means of a membrane located in the air passage. In this way, the air-borne terms can be effectively restricted. Furthermore, the air can be guided past absorbent or absorptive materials which trap the air-borne germs on its way in. In this method, electrostatic forces especially can be used. Furthermore, the degermination of the air can also be achieved by using oligodynamically effective substances arranged in the inward path of the air. It is also important that these means can be combined, e.g. germs are absorbed by agents which also have microbicidal properties.

A further advantage produced by the separate degermination of the fluid and the air is that substances used for sterilising the air do not come into contact with the fluid. This prevents any foreign substances passing into the fluid and therefore prevents the consumer from being confronted with these substances.

The dispensing apparatus can be a pump which is placed on top of a conventional storage vessel. The paths of the outgoing fluid and incoming air which are, at least in one part, guided separately, can be integrated into the pump.

Furthermore, the storage vessel can be designed as a squeezy bottle for dispensing the fluid. In this case, a valve is provided at the fluid outlet to improve the favourability of this embodiment.

In the following, exemplified embodiments of the present invention will be explained in detail with the help of the attached drawings.

Figure 1:
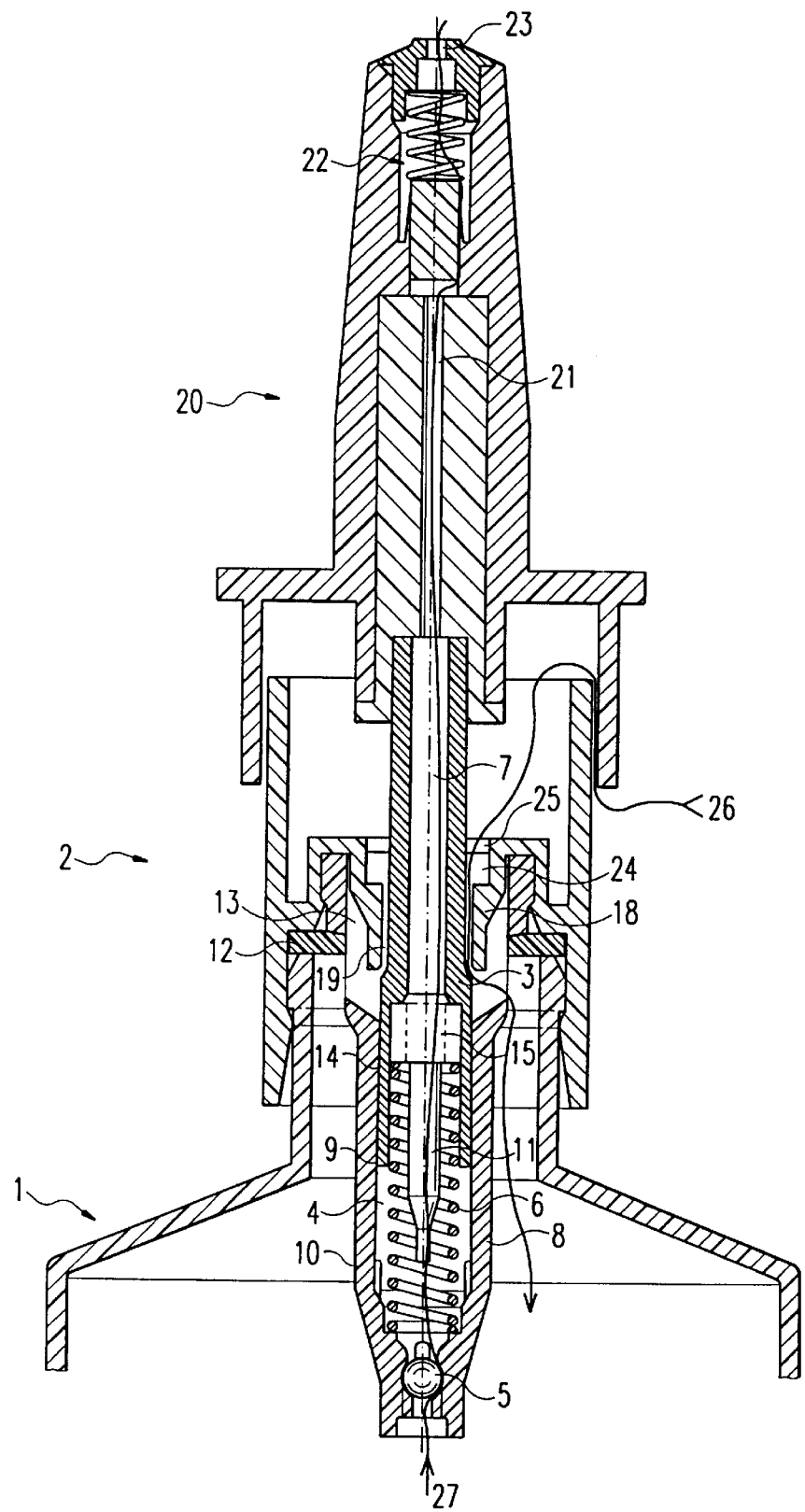
FIG. 1 shows, as an example, a dispensing apparatus in which means are used for degerminating the fluid and, in a separate process, for degerminating the inflowing air.
Figure 2:
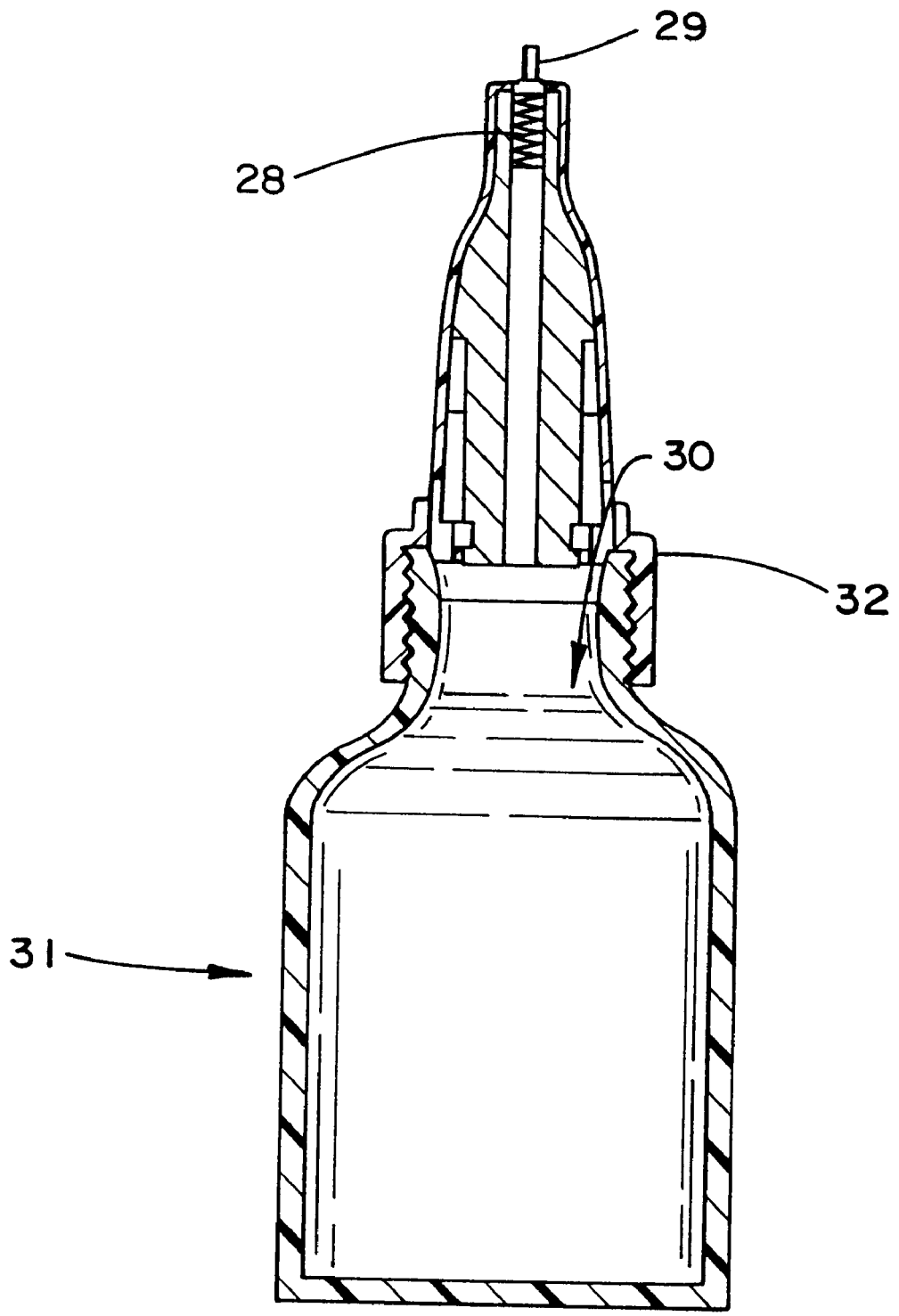
FIG. 2 shows a further exemplified embodiment in which the storage vessel is formed as a squeezy bottle as the dispensing apparatus.

In a first embodiment illustrated in FIG. 1, a suction/pressure pump 2 is used whose construction is demonstrated by the drawing. The suction/pressure pump 2 is placed tightly on top of the (only partially illustrated) fluid storage vessel 1 by means of the conical nipple 12. A piston 3 with an axial pump channel 7 works in the pressure cylinder 8. The piston 3 is held in its upper resting position by a spring 6 on a stopper. The pressure chamber 4, which is connected to the axial pumping channel 7, is located between the piston 3 and the ball valve 5. The piston 3 has a smaller outer diameter than the inner diameter of the pressure cylinder 8 so that a gap 14 remains between the outer wall of the piston and the inner wall of the cylinder which is however sealed further downwards by the peripheral sealing lip 9 of the piston. In the bottom region of the pressure chamber 4, the pressure cylinder 8 has a section 10 with a larger inner diameter in which the sealing lip 9 does not have a sealing effect. An actuation element 20 placed on the piston 3 has an ascending pipe 21 with a pressure control valve 22 for dispensing the fluid through an outlet 23. When the piston 3 is in its upper position of rest as illustrated in the drawing, the sealing lip 9 seals the pressure chamber 4 off from the openings 13 to the fluid vessel. The tappet 11 is fixedly connected to the piston 3 with the section 15 having a star-shaped cross-section leaving spare a connection between pressure chamber 4 and pump channel 7. When the pump is at rest, the tappet 11 is distanced from the ball valve 5 so that this valve opens the fluid vessel 1 when there is excess pressure in pressure chamber 4 and closes it when low pressure is present. The path of the fluid from the fluid vessel 1 through the dispensing apparatus 2 is diagrammatically illustrated by the arrow beginning by 27. When the ball valve 5 is open, the fluid passes through the valve into the pump channel 7 and passes through the open pressure valve control 22 to the outlet 23. In order to prevent contamination of the fluid stored in the fluid container 1, oligodynamically effective substances are arranged on the outward path of the fluid described above. Thus, these substances can be arranged for example on the spring 6, the inner walling of the pump channel 7, in the pressure valve control 22 or on the outlet 23.

For compensating pressure in the fluid vessel 1 when dispensing the fluid, air enters the dispensing apparatus from the surroundings at 26 and then passes into fluid vessel 1 as illustrated by the arrow in the drawing. A gap 19 is located on at least one part of the range between the piston 3 and the section 18. Means for degerminating the incoming air are provided in the area of the path for incoming air which sterilise air. Possible means for doing so are a sterile filter, a membrane through which the air passes by permeation, germ-absorbing or germ-absorptive materials, oligodynamically effective or microbicidal substances and combinations thereof. For example, a sterile filter 25 which the air must pass through on its way in can be arranged in the region 24. Furthermore, the very narrowly formed gap 19 is suitable for applying, for example, metallic silver as an oligodynamically effective substance.

In a further embodiment illustrated in FIG. 2, the fluid is dispensed by a squeezy bottle 31. The fluid is dispensed through the fluid outlet 29 by squeezing the squeezy bottle 31. A valve 28, for example a check valve, is provided on the fluid outlet 29. Agents for degerminating or reducing the germs in the fluid are provided in this valve in the parts in contact with the fluid. Furthermore, the dispensing apparatus in this exemplified embodiment has an air inlet 30 guided separately from the fluid outlet 29. Means 32 for sterilising, degerminating or reducing the germs in the incoming air are also provided at the air inlet 30. For the degermination of the air, a sterile filter 32 can, for example, be used and for the reduction in germs in or the degermination of the fluid, substances like, for example, silver can be used which have an oligodynamic effect.

It should be emphasised that the degermination of the fluid is carried out separately from the degermination of the air. This means that it is possible to provide and selectively use different means for air and fluid degermination. In addition, the disposing apparatus exemplified in these embodiments are designed such that they can be adapted to any conventional storage vessel and various pump versions for dispensing vertically and horizontally can be converted to use this system.

The fluid in the storage vessel is efficiently protected from contamination in a manner which is good value for money so that preservatives are superfluous. Preservatives are dubious substances and lead to undesireable side effects.

I claim:

1. A dispensing apparatus for fluids from a storage vessel in which a fluid is dispensed through a fluid outlet with the aid of a pump and in which, while the fluid is being dispensed, air flows into the storage vessel through an air inlet which surrounds the pump, and in which a sterile filter is provided for sterilizing, degerminating or reducing germs present in the air to achieve pressure compensation, wherein in a fluid outlet area, surfaces or apparatus which come into contact with the fluid are provided with substances which have an oligodynamic effect or germ-reducing properties for sterilizing, degerminating or reducing the germs in the fluid, the air inlet is formed by a narrow gap between at least one part of the periphery of a piston of the pump and a casing section, and wherein the sterile filter is arranged within the gap between the periphery of the piston and the casing section.

2. A dispensing apparatus according to claim 1, wherein the oligodynamically effective substances are selectively a heavy metal and a heavy metal alloy which is effective in selectively metallic and ionic form.

3. A dispensing apparatus according to claim 1, wherein said oligodynamically effective substances consist of silver.

4. A dispensing apparatus according to claim 1, wherein differing means are provided for sterilizing, degerminating or reducing germs in the air and in the fluid.

5. A dispensing apparatus according to claim 1, wherein metallic silver is arranged as an oligodynamically effective substance in said narrow gap.

6. A dispensing apparatus according to claim 1, wherein agents for degerminating the incoming air in the sterile filter consist of oligodynamically effective substances.

7. A dispensing apparatus according to claim 2, wherein agents for degerminating the incoming air in the sterile filter consist of oligodynamically effective substances.

8. A dispensing apparatus according to claim 4, wherein agents for degerminating the incoming air in the sterile filter consist of oligodynamically effective substances.

9. A dispensing apparatus according to claim 5, wherein agents for degerminating the incoming air in the sterile filter consist of oligodynamically effective substances.

* * * * *